United States Patent [19]

Tartaglia

[11] Patent Number: 4,518,386
[45] Date of Patent: May 21, 1985

[54] MEDICINE CONTAINER HAVING LYOPHILIZED POWDER AND DILUENT STORED IN SEPARATE SEALED CHAMBERS

[76] Inventor: John A. Tartaglia, 101 Pierpont Rd., Waterbury, Conn. 06705

[21] Appl. No.: 527,980

[22] Filed: Aug. 31, 1983

[51] Int. Cl.³ .............................................. A61M 5/00
[52] U.S. Cl. ..................... 604/89; 604/191; 206/219; 215/6
[58] Field of Search ............... 604/89, 90, 191, 218, 604/220, 221, 228; 206/219; 215/6

[56] References Cited

U.S. PATENT DOCUMENTS

| | | | |
|---|---|---|---|
| 2,841,145 | 7/1958 | Epps | 604/89 |
| 3,477,431 | 11/1969 | Walecka | 604/89 |
| 3,511,239 | 5/1970 | Juschhoff | 604/89 |
| 3,662,753 | 5/1972 | Tassell | 604/89 |

*Primary Examiner*—Stephen C. Pellegrino

[57] ABSTRACT

A medical device employs a first elongated hollow cylinder having a first inner diameter, one end of the first cylinder being open, the other end of the first cylinder removably receiving a hypodermic needle and being otherwise sealed. The device also employs a second elongated hollow cylinder having a second and smaller inner diameter, the first and second cylinders being disposed end to end along a common axis, one end of the second cylinder being open and disposed adjacent the one end of the first cylinder, the other end of the second cylinder being adapted to be detachably engaged by a cylinder engaging member. The device also employs a sealing member disposed between and detachably engaging both cylinders, the member having a first cylindrical section having a diameter slightly smaller than said first diameter and disposed in slidable sealing engagement in the one end of the first cylinder, the member having a second cylindrical section having a diameter slightly smaller than the second cylinder and disposed in slidable sealing engagement in the one end of the second cylinder, the first section having a first coefficient of friction with respect to the inner wall of the first cylinder, the second section having a second and higher coefficient of friction with respect to the inner wall of the second cylinder; A first medicine is disposed in the first cylinder; A second medicine is disposed in the second cylinder.

7 Claims, 6 Drawing Figures

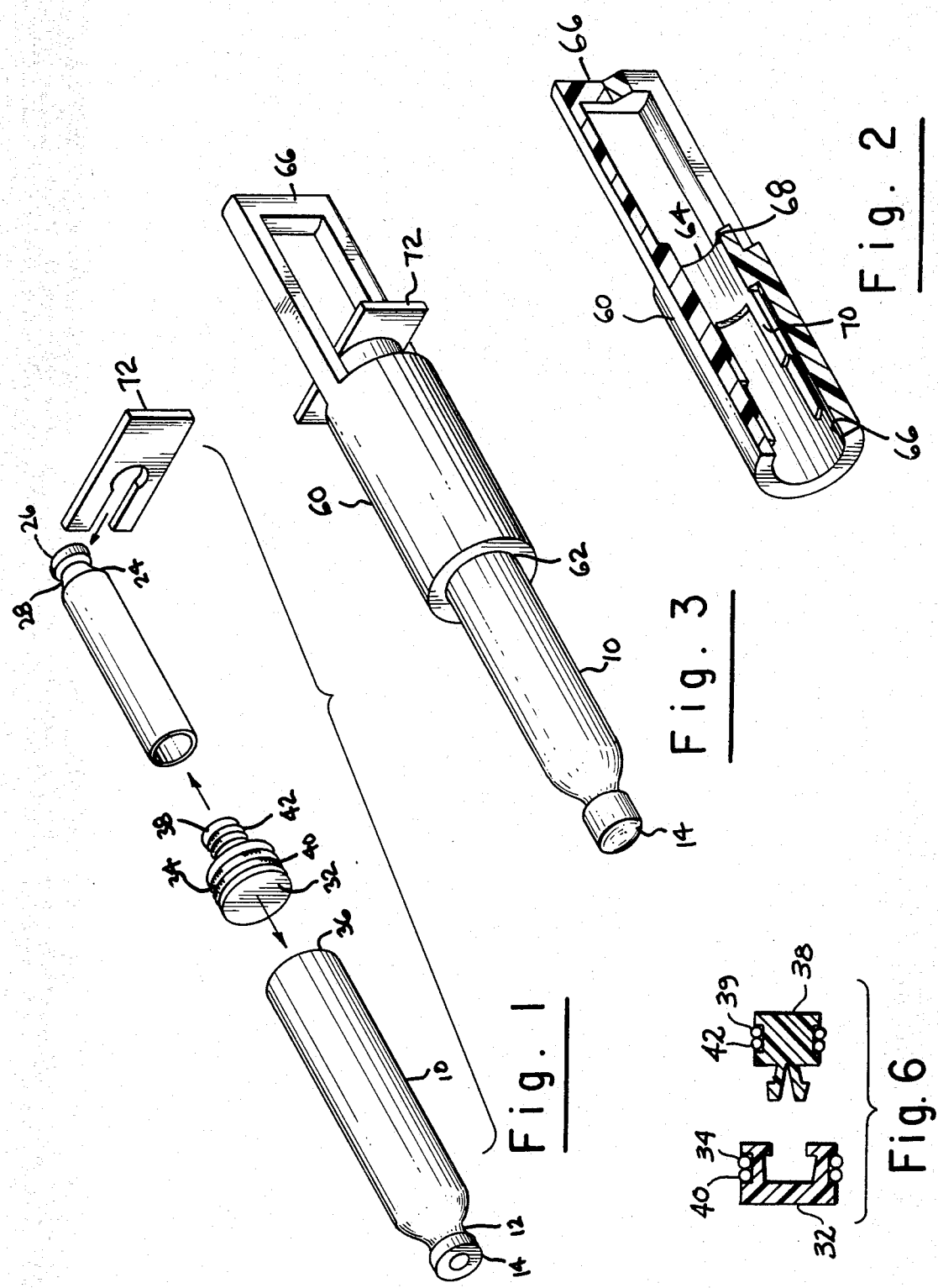

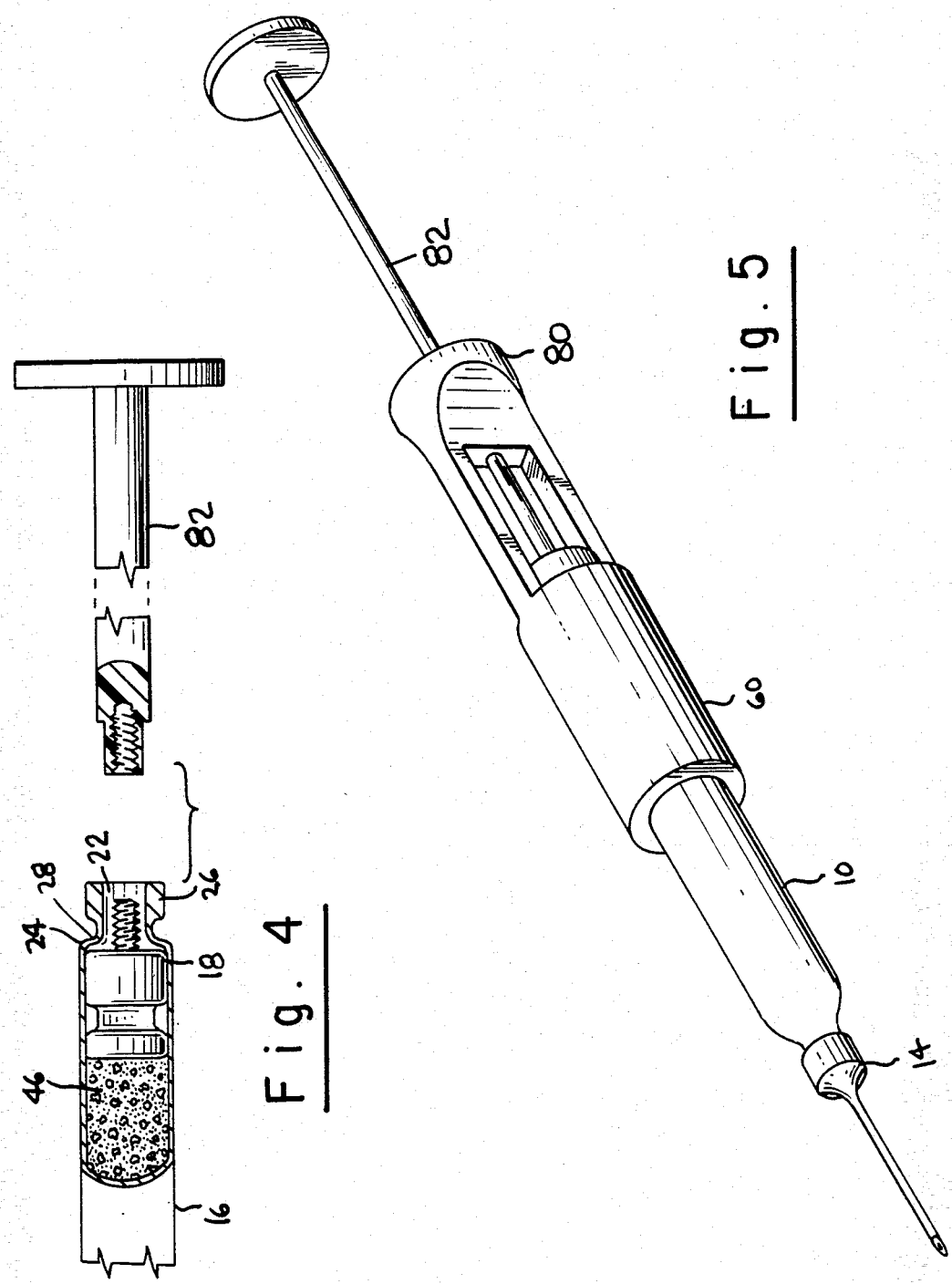

MEDICINE CONTAINER HAVING LYOPHILIZED POWDER AND DILUENT STORED IN SEPARATE SEALED CHAMBERS

BACKGROUND OF THE INVENTION

Certain medicines which must be administered to patients by injection consist of lyophilized powder dissolved in a diluent. The powder and diluent must be mixed together immediately before use, since if the powder and diluent are mixed at an earlier time, the medicine will deteriorate rapidly.

Conventionally the powder and diluent are mixed at time of dosage and the medicine is transferred into a syringe for immediate subsequent injection.

The present invention is directed toward a new type of medical device wherein the powder and diluent can be stored in separate sealed chambers of an integral unit for indefinite periods and wherein the unit itself can be disposed either in a mixer for immediate mixing and transfer to a syringe or in a syringe wherein mixing can ensue immediately before injection.

SUMMARY OF THE INVENTION

In accordance with the principles of this invention, a first elongated hollow cylinder is employed. This first cylinder has a first inner diameter. One end of the first cylinder is open; the other end is provided with means for receiving a hypodermic needle and is otherwise sealed.

A second elongated hollow cylinder is also employed. The second cylinder has a second and smaller inner diameter. The first and second cylinders are disposed end to end along a common axis. One end of the second cylinder is open and disposed adjacent said one end of the first cylinder. The other end of the second cylinder is adapted to be detachably engaged by cylinder engaging means.

A sealing member is disposed between and detachably engaging both cylinders. This member has a first cylindrical section having a diameter slightly smaller than said first diameter which is disposed in slidable sealing engagement in said one end of the first cylinder. This member also has a second cylindrical section having a diameter slightly smaller than said second cylinder which is disposed in slidable sealing engagement in said one end of the second cylinder. The first section has a first coefficient of friction with respect to the inner wall of the first cylinder, said second section having a second and higher coefficient of friction with respect to the inner wall of the second cylinder. The two sections of the member are detachably engagable but are engaged when the invention is placed in use.

A first medicine, for example lyophilized powder, is disposed in the first cylinder. A second medicine, for example a diluent, is disposed in the second cylinder.

A mixer device can be used to mix the diluent and power. The mixer device can take the form of a vertical hollow housing having upper and lower open ends interconnected by a cylindrical bore. The two cylinder structure is inserted in the bore with the first cylinder being disposed below the second cylinder. The other end of the second cylinder is disposed in sliding sealing engagement with the upper end of the housing. The end of the first cylinder which contains the first section of the sealing member is disposed within and is sealed in fixed relationship to the lower end of the housing. The other end of the first cylinder protrudes below the housing.

Cylinder engaging means can be detachably engaged to the other end of the second cylinder to pull it upwardly through the upper end of the housing. As this action takes place, since the sealing member is initially free to move upward, the first section is pulled out of the first cylinder. The difference in the coefficients of friction ensures that the first section of the member is pulled out of the first cylinder while the second section remains in position in the second section. There is clearance space between the periphery of the first section and the wall of the bore.

A construction in the bore disposed between the two ends blocks further movement upward of the first section and has an opening large enough to permit the second cylinder to pass upwardly therethrough. As the second cylinder passes therethrough, the second section of the member is pulled out of the second cylinder.

The clearances are such that the diluent flows out of the second cylinder through the constriction and around the member into the first cylinder to mix with the powder.

The engaging means can then be used to push the second cylinder downwardly and cause the member to reengage both cylinders if desired. A syringe can then be used to open the means for receiving a hypodermic needle and to aspirate the mixture from the second cylinder into the syringe for subsequent use.

Alternatively the engaging means can be a plunger whereby after a hypodermic needle is connected to the needle receiving means the mixer is converted to a syringe and the mixture can be injected directly by pushing the plunger into the housing. This action pushes the sealing member into the first cylinder and forces the mixture out of the needle.

Since the two sections of the sealing member are detachably engagable, each cylinder can have its corresponding medicine disposed therein and sealed with the corresponding section. Each cylinder so sealed can be stored separately. Alternatively, the two cylinders can be interconnected via each section when the two sections are engaged and the entire structure can be stored as a unit.

BRIEF DESCRIPTION OF THE DRAWINGS

FIG. 1 is a perspective view showing the first and second cylinders and sealing member.

FIG. 2 is a view of a mixer housing used in the invention.

FIG. 3 illustrates the use of the mixer housing with the cylinders and sealing members disposed therein.

FIG. 4 is a view of a syringe structure used in the invention.

FIG. 5 illustrates the use of the syringe structure with the cylinders and sealing members disposed therein.

FIG. 6 illustrates the two sections of the sealing member.

DETAILED DESCRIPTION OF THE PREFERRED EMBODIMENTS

Referring now to FIG. 1, a hollow elongated glass cylinder 10 having a first inner diameter has one end 12 sealed except for a small protrusion 14 which is sealed and which can detachably receive a hypodermic needle. The opposite end 36 of the cylinder 10 is open.

A second hollow elongated glass cylinder 16 has a second and smaller inner diameter. One end 24 of the cylinder 16 carries an inner seal 18 having a threaded bore 20 accessible via an opening 22 in the end 24. End 24 also carries a protrusion 26 with an outer circular groove 28. The opposite end 30 of the cylinder 16 is open.

A sealing member of glass has a first cylindrical section 32 which has a circular outer groove 34 having O ring seals 40 and which is in slidable sealing engagement with end 36 of cylinder 10. This member has a second cylindrical section 38 which has a circular outer groove 39 having O ring seals 42 and which is in slidable sealing engagement with end 30 of cylinder 16. The diameters of the O ring seals 40 and 42 and the depth of grooves 34 and 39 are so adjusted that the coefficient of friction between section 32 and the inner wall of cylinder 10 is lower than the coefficient of friction between section 38 and the inner wall of cylinder 16.

A first medicine such as lyophilized powder 44 can be placed in cylinder 10 while a second medicine such as diluent 46 can be placed in cylinder 16. The cylinders are disposed end to end along a common axis.

Referring now to FIGS. 2 and 3 a glass housing 60 has a U shaped handle 66 at one end, a first relatively large open end 62 remote from the handle and a second relatively small open end 64 adjacent the handle. The housing has a cylindrical bore 66 which extends between the two ends. A constriction 68 in the housing adjacent end 64 has a central opening coincident with that of end 64. Spaced apart ribs 70 extend axially along the wall of the bore between the constriction and an end position spaced from but adjacent to end 62. Halfway along each rib, its depth changes. The rib has a first depth or thickness between the constriction and the midpoint which is uniform but thicker than the thickness which is thinner and also uniform between the midpoint and the end position.

The first cylinder 10 is disposed within the housing until end 36 abuts the end position of the ribs and the cylinder is then sealed in place by cement. The thickness of the ribs between the end position and the halfway point is such that the section 32 when pulled out of the first cylinder can be slid along to the midpoint where it is blocked and can pass no further.

The second cylinder is slidable in the bore through the opening in the constriction when clip 72 engages groove 28 in end 24 and is moved manually away from the cylinder 10 within the handle. This first causes section 32 to be pulled out of the cylinder 10, then as section 32 engages the midpoint of the ribs, section 38 is pulled out of cylinder 16.

If the structure is disposed vertically with cylinder 10 below cylinder 16, the mixing action will take place between diluent and powder. The clip movement can be reversed to reconnect the sections and cylinders. The seal at protrusion 16 can then be broken and the mixture aspirated as before.

Referring now to FIGS. 4 and 5, housing 60 has a U shaped handle at one end having an enlarged head 80 with a central bore. The interior of housing 60 is as shown in FIGS. 2 and 3 and the cylinders are disposed therein in the same manner. However, clip 72 is replaced by a plunger 82 having one end which threadedly engages bore 20 of seal 18. As the plunger is withdrawn, the mixing action takes place as before. Then if the seal at protrusion 16 is broken and a hypodermic needle is secured thereto, a syringe is formed and injection can occur in usual manner by reversing the motion of the plunger.

If the relationship of the coefficients of friction is reversed, the second section will separate from the second cylinder before the first section is pulled out of the first cylinder and the desired mixing action cannot ensue.

The sections of the sealing member are detachably engagable as shown in FIG. 6.

WHAT IS CLAIMED IS:

1. A medical device comprising:
   a first elongated hollow cylinder having a first inner diameter, one end of the first cylinder being open, the other end of the first cylinder being provided with means for receiving a hypodermic needle and being otherwise sealed;
   a second elongated hollow cylinder having a second and smaller inner diameter, the first and second cylinders being disposed end to end a long a common axis, one end of the second cylinder being open and disposed adjacent said one end of the first cylinder, the other end of the second cylinder being adapted to be detachably engaged by cylinder engaging means;
   a sealing member disposed between and detachably engaging both cylinders, said member having a first cylindrical section having a diameter slightly smaller than said first diameter with means disposed in slidable sealing engagement in said one end of the first cylinder, said member having a second cylindrical section having a diameter slightly smaller than said second cylinder with means disposed in slidable sealing engagement in said one end of the second cylinder, said first section means having a first coefficient of friction with respect to the inner wall of the first cylinder, said second section means having a second and higher coefficient of friction with respect to the inner wall of the second cylinder;
   a first medicine disposed in the first cylinder; and
   a second medicine disposed in the second cylinder.

2. The device of claim 1 further including cylinder engaging means detachably engaging the other end of the second cylinder whereby when said first cylinder is held in fixed position and said cylinder engaging means is moved along said axis away from the first cylinder, the sealing member first section is pulled out of the first cylinder as the second cylinder is pulled away from the first cylinder.

3. The device of claim 2 further including member restraining means for preventing further movement of said member while permitting further movement of the second cylinder whereby as the cylinder engaging means is moved further along the axis away from the first cylinder, the sealing member second section is pulled out of the second cylinder.

4. The device of claim 3 further including a housing supporting said cylinder engaging means, said member retaining means, said first cylinder being secured to said housing in sealed fixed relationship, said second cylinder being disposed in sealed sliding relationship in said housing.

5. The device of claim 1 further including a housing having a cylindrical inner bore aligned with said common axis and having two opposite open ends, said first and second cylinders being disposed partially within said bore, said first cylinder being sealed in fixed position in one of the ends of the housing, the second cylinder being sealed slidably in the other end of the housing, the said other end of the first cylinder being disposed outside of the housing; first means in said housing for permitting said first section of the sealing member to be pulled out of the first cylinder and to be moved a predetermined distance along the axis from the one end of the first cylinder toward the other end of the housing, said first means blocking further movement of said first section beyond said distance while permitting movement of said second cylinder therethrough.

6. The device of claim 1 wherein the first and second sections of the sealing member are detachably engagable.

7. A medical device comprising:
a first elongated hollow vertical cylinder having a first inner diameter, the upper end of the first cylinder being open, the lower end of the first cylinder being provided with means for receiving a hypodermic needle and being otherwise sealed;
a second elongated hollow vertical cylinder having a second and smaller inner diameter, the first and second cylinders being disposed end to end along a common axis, with the second cylinder being disposed above the first cylinder, the lower end of the second cylinder being open and disposed adjacent the upper end of the first cylinder, the upper end of the second cylinder being adapted to be detachably engaged by cylinder engaging means;
a sealing member disposed between and detachably engaging both cylinders, said member having a first cylindrical section having a diameter slightly smaller than said first diameter with means disposed in slidable sealing engagement in said one end of the first cylinder, said member having a second cylindrical section having a diameter slightly smaller than said second cylinder with means disposed in slidable sealing engagement in said one end of the second cylinder, said first section means having a first coefficient of friction with respect to the inner wall of the first cylinder, said second section means having a second and higher coefficient of friction with respect to the inner wall of the second cylinder;
a first medicine disposed in the first cylinder;
a second medicine disposed in the second cylinder; and a vertical hollow housing having oppositely disposed open upper and lower open ends and a cylindrical bore extending therebetween, the upper end of the first cylinder being sealed to the lower end of the housing, the upper end of the second cylinder being accessible at the upper end of the housing, said bore having a constriction intermediate its ends, said first section being slidable in the bore between the lower end of the housing and the constriction, said second cylinder being slidable along the entire bore through said constriction.

* * * * *